United States Patent
Ota et al.

(10) Patent No.: US 12,239,473 B2
(45) Date of Patent: Mar. 4, 2025

(54) MAMMOGRAPHY APPARATUS

(71) Applicant: FUJIFILM Corporation, Tokyo (JP)

(72) Inventors: Kohei Ota, Kanagawa (JP); Takeyasu Kobayashi, Kanagawa (JP); Sayaka Saito, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 64 days.

(21) Appl. No.: 18/457,289

(22) Filed: Aug. 28, 2023

(65) Prior Publication Data
US 2024/0065650 A1 Feb. 29, 2024

(30) Foreign Application Priority Data
Aug. 30, 2022 (JP) .................. 2022-137270

(51) Int. Cl.
- *A61B 6/50* (2024.01)
- *A61B 6/00* (2024.01)
- *A61B 6/04* (2006.01)

(52) U.S. Cl.
CPC .......... *A61B 6/0435* (2013.01); *A61B 6/4452* (2013.01); *A61B 6/4476* (2013.01); *A61B 6/502* (2013.01); *A61B 6/0414* (2013.01)

(58) Field of Classification Search
CPC ...... A61B 6/4452; A61B 6/4476; A61B 6/502
See application file for complete search history.

(56) References Cited

U.S. PATENT DOCUMENTS

| | | | |
|---|---|---|---|
| 6,999,554 B2* | 2/2006 | Mertelmeier | A61B 6/56 378/197 |
| 2007/0183566 A1* | 8/2007 | Tsujita | A61B 6/56 378/37 |
| 2013/0301796 A1* | 11/2013 | Kim | A61B 6/56 396/419 |

FOREIGN PATENT DOCUMENTS

| | | | |
|---|---|---|---|
| DE | 102019212066 A1 * | 2/2021 | ........... A61B 6/0414 |
| JP | 2007-236805 A | 9/2007 | |

OTHER PUBLICATIONS

The extended European search report issued by the European Patent Office on Jan. 11, 2024, which corresponds to European Patent Application No. 23194007.3-1126 and is related to U.S. Appl. No. 18/457,289.

* cited by examiner

*Primary Examiner* — Colin T. Sakamoto
(74) *Attorney, Agent, or Firm* — Studebaker & Brackett PC

(57) ABSTRACT

A mammography apparatus includes an arm; and a stand, the arm is provided with a drive mechanism including a motor that rotationally drives the radiation source holding portion, and a first restriction mechanism that restricts rotation of the imaging table about the axis of the support shaft, the first restriction mechanism is disposed on a side opposite to a radiation source with respect to the support shaft, and the drive mechanism is disposed on a radiation source side with respect to the first restriction mechanism and in a case where a center line of the arm extending in a direction connecting the radiation source and a center of the support shaft is assumed, the drive mechanism is disposed so as to intersect the center line.

9 Claims, 11 Drawing Sheets

MAMMOGRAPHY APPARATUS

CROSS-REFERENCE TO RELATED APPLICATION

This application claims priority from Japanese Patent Application No. 2022-137270, filed Aug. 30, 2022, the disclosure of which is incorporated herein by reference in its entirety.

BACKGROUND

Technical Field

The present disclosure relates to a mammography apparatus.

Related Art

JP2007-236805A discloses an X-ray diagnostic apparatus for mammography, which is composed of an arm portion and a support column portion. The arm portion is provided with an X-ray source device, a plane detector, and a compression plate that are installed facing each other. In addition, the support column portion is provided with a display panel, a foot pedal, and a touch panel. The arm portion can move up and down with respect to the support column portion and can move rotationally about a shaft.

However, in the technology disclosed in JP2007-236805A, an arrangement of a drive mechanism for rotating an arm and a restriction mechanism for restricting the rotation of the arm is not described. For example, in a case where the drive mechanism and the restriction mechanism are disposed in the arm, depending on a position of a center of gravity with respect to a rotation center, the center of gravity is biased, and a rotational moment of the arm around a support shaft increases. As a result, a load applied to the drive mechanism may increase with the rotation of the arm.

SUMMARY

The technology of the present disclosure provides a mammography apparatus capable of reducing a rotational moment of an arm in a case where a drive mechanism and a restriction mechanism are disposed in the arm.

A first aspect according to the technology of the present disclosure is a mammography apparatus comprising: an arm composed of a radiation source holding portion that holds a radiation source, and an imaging table on which a breast is placed; and a stand that is connected to the arm via a support shaft and supports the arm to be rotatable about an axis of the support shaft, in which the arm is capable of rotating the radiation source holding portion with respect to the imaging table by rotating the radiation source holding portion about the axis of the support shaft independently of the imaging table, the arm is provided with a drive mechanism including a motor that rotationally drives the radiation source holding portion, and a first restriction mechanism that restricts rotation of the imaging table about the axis of the support shaft, the first restriction mechanism is disposed on a side opposite to the radiation source with respect to the support shaft, and the drive mechanism is disposed on a radiation source side with respect to the first restriction mechanism and in a case where a center line of the arm extending in a direction connecting the radiation source and a center of the support shaft is assumed, the drive mechanism is disposed so as to intersect the center line.

A second aspect according to the technology of the present disclosure is the mammography apparatus according to the first aspect, in which the motor and the center line intersect each other.

A third aspect according to the technology of the present disclosure is the mammography apparatus according to the first aspect, in which in a direction of the center line, a shortest distance between the drive mechanism and the center of the support shaft is shorter than a shortest distance between the drive mechanism and the radiation source.

A fourth aspect according to the technology of the present disclosure is the mammography apparatus according to the first aspect, in which the motor and the first restriction mechanism are disposed at positions facing each other with the support shaft interposed therebetween.

A fifth aspect according to the technology of the present disclosure is the mammography apparatus according to the first aspect, in which the drive mechanism has a longitudinal direction and is disposed in a posture in which the longitudinal direction is inclined with respect to the center line.

A sixth aspect according to the technology of the present disclosure is the mammography apparatus according to the first aspect, in which the drive mechanism is accommodated in the radiation source holding portion, and at least a part of the first restriction mechanism is accommodated in the radiation source holding portion.

A seventh aspect according to the technology of the present disclosure is the mammography apparatus according to the fifth aspect, in which the radiation source holding portion has a housing that accommodates the radiation source and the drive mechanism, in a case where the housing is viewed from a direction in which the support shaft extends, a width of the housing in a direction orthogonal to the center line is narrowed from a support shaft side toward the radiation source side, and an intersection position where the drive mechanism intersects the center line is located on the radiation source side with respect to a center position in the longitudinal direction.

An eighth aspect according to the technology of the present disclosure is the mammography apparatus according to the first aspect, in which an elevating mechanism for raising and lowering the arm is disposed in the stand.

A ninth aspect according to the technology of the present disclosure is the mammography apparatus according to the first aspect, in which the arm is further provided with a second restriction mechanism that restricts rotation of the radiation source holding portion with respect to the imaging table and that is disposed on a side opposite to the radiation source with respect to the support shaft.

According to the technology of the present disclosure, it is possible to provide a mammography apparatus capable of reducing a rotational moment of an arm in a case where a drive mechanism and a restriction mechanism are disposed in the arm.

DETAILED DESCRIPTION

Hereinafter, an embodiment of the present disclosure will be described in detail with reference to the drawings.

In the following description, for convenience of explanation, a height direction, a width direction, and a front-rear direction (also referred to as a depth direction) of the mammography apparatus 10 are indicated by three arrows X, Y, and Z. First, the height direction is indicated by the arrow Z, an arrow Z direction pointed by the arrow Z is an upward direction of the mammography apparatus 10, and an opposite direction of the upward direction is a downward direction. The height direction is a vertical direction. The width direction is indicated by the arrow X orthogonal to the arrow Z, a direction pointed by the arrow X is a right direction of the mammography apparatus 10, and an opposite direction of the right direction is a left direction. The front-rear direction is indicated by the arrow Y orthogonal to the arrow Z and the arrow X, a direction pointed by the arrow Y is a frontward direction of the mammography apparatus 10, and an opposite direction of the frontward direction is a rearward direction. That is, in the mammography apparatus 10, a stand 20 side is the rearward direction, and an opposite side thereof on which a subject A stands (see FIG. 2) is the frontward direction. In addition, in the following, expressions using sides such as an upper side, a lower side, a left side, a right side, a front side, and a rear side have the same meanings as the expressions using the directions.

In the present embodiment, a "vertical direction" refers not only to a perfect vertical direction but also to a vertical direction in the sense of including an error that is generally acceptable in the technical field to which the technology of the present disclosure belongs and that does not contradict the concept of the technology of the present disclosure. The same applies to a "horizontal direction". The "horizontal direction" refers not only to a perfect horizontal direction but also to a horizontal direction in the sense of including an error that is generally acceptable in the technical field to which the technology of the present disclosure belongs and that does not contradict the concept of the technology of the present disclosure.

Figure 1:
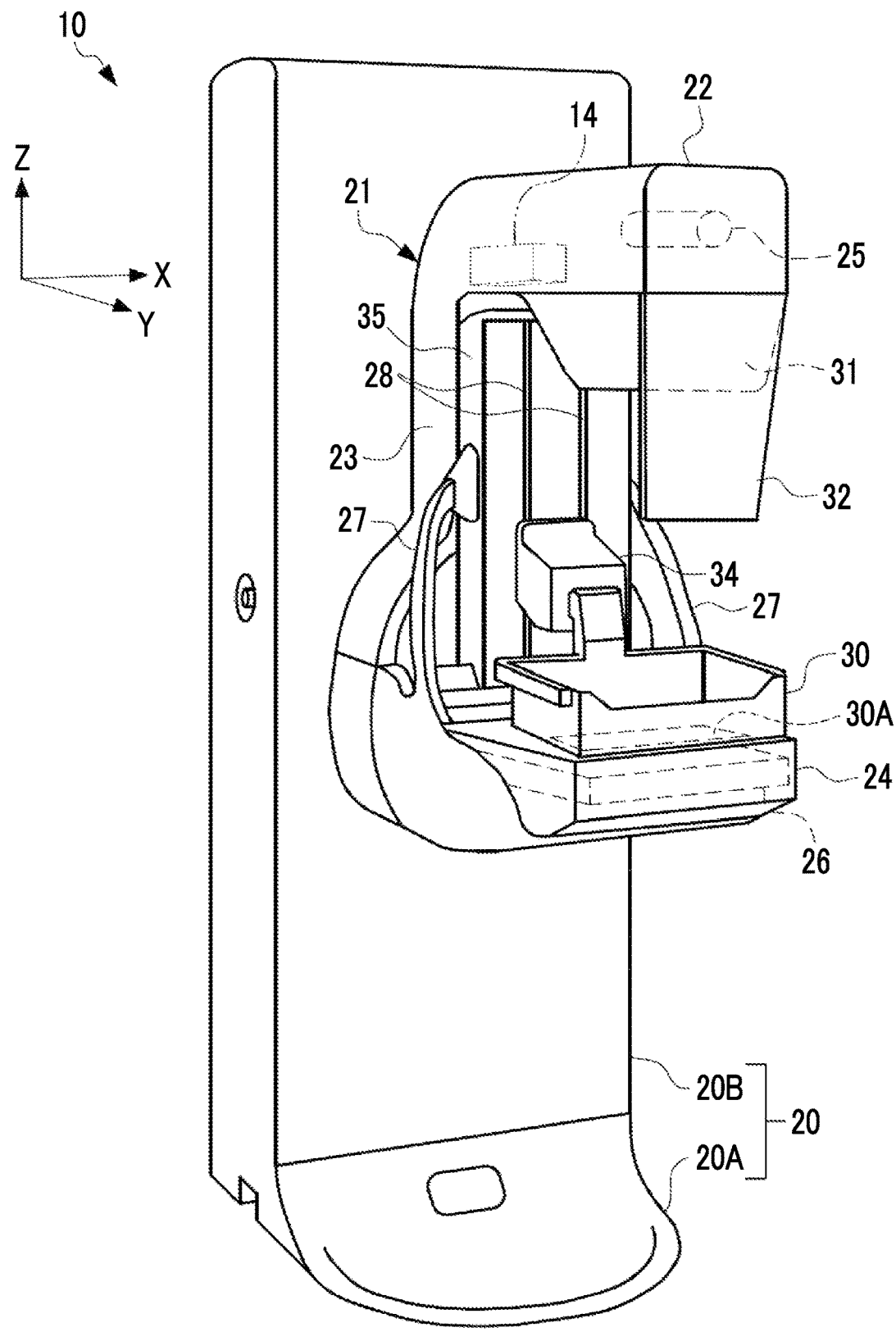
FIG. 1 is an external perspective view showing an example of a configuration of a mammography apparatus.
Figure 2:
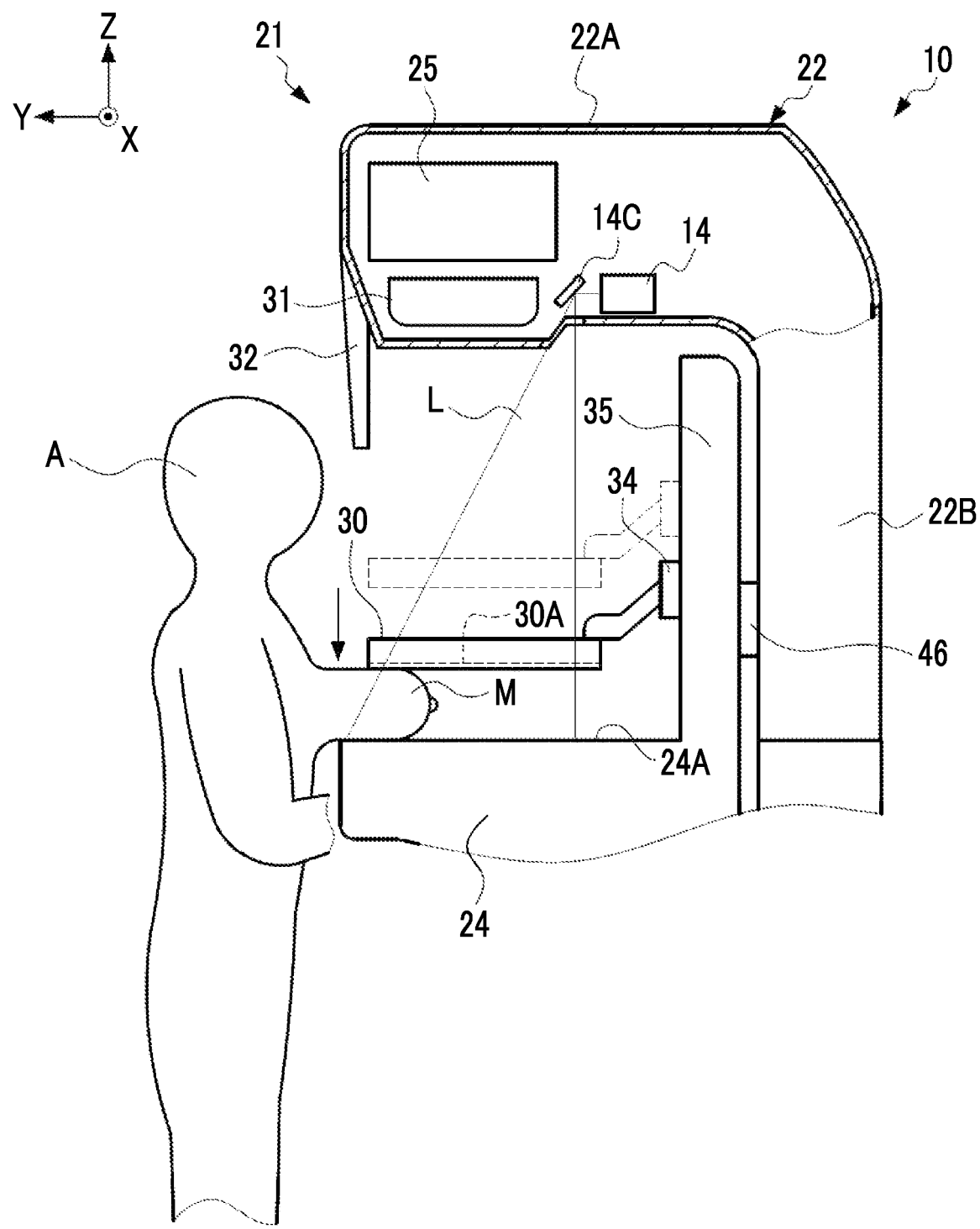
FIG. 2 is an external side view showing an example of the configuration of the mammography apparatus.

As shown in FIGS. 1 and 2, the mammography apparatus 10 according to a first embodiment is a radiography apparatus that irradiates a breast M of the subject A to be examined with radiation and captures a radiographic image of the breast M. The radiation is X-rays as an example, but y-rays may also be used. The subject A is located on the front side with respect to the mammography apparatus 10. The mammography apparatus 10 is an example of a "mammography apparatus" according to the technology of the present disclosure.

The mammography apparatus 10 is connected to a console (not shown). The console has a setting function of setting the mammography apparatus 10 in accordance with an imaging order and a function of acquiring a radiographic image captured by the mammography apparatus 10 and displaying the acquired radiographic image. The console is communicably connected to an image database server (not shown) via a network (not shown) such as a local area network (LAN).

The mammography apparatus 10 includes a stand 20 and an arm 21. The stand 20 includes a pedestal 20A that is provided on a floor of a radiography room and a support column 20B that extends from the pedestal 20A in a height direction. The arm 21 has a substantially C-shape as viewed from the left and is connected to the support column 20B via a support shaft 46 (see FIG. 3). Since the arm 21 is movable in a height direction with respect to the support column 20B, a height of the arm 21 can be adjusted according to a height of the subject A. In addition, the arm 21 is rotatable about the support shaft 46 (see FIG. 3) perpendicular to the support column 20B. The stand 20 is an example of a "stand" according to the technology of the present disclosure. The arm 21 is an example of an "arm" according to the technology of the present disclosure.

The arm 21 is composed of a radiation source holding portion 22 and an imaging table 24. The radiation source holding portion 22 has an L-shape in a case where the mammography apparatus 10 is viewed from a right side surface. The radiation source holding portion 22 comprises a radiation source accommodation portion 22A and a connection portion 22B. The radiation source accommodation portion 22A is a portion of the radiation source holding portion 22 along the horizontal direction (Y direction shown in FIG. 2) and is provided with a radiation source 25. The connection portion 22B is a portion of the radiation source holding portion 22 along the vertical direction (Z direction shown in FIG. 2) and is connected to the imaging table 24 via the support shaft 46 (see FIG. 3). The radiation source holding portion 22 is an example of a "radiation source holding portion" according to the technology of the present disclosure.

The radiation source 25 is accommodated in the radiation source accommodation portion 22A. The connection portion 22B integrally connects the radiation source accommodation portion 22A and the imaging table 24. The connection portion 22B holds the radiation source accommodation portion 22A and the imaging table 24 at positions facing each other. In this way, the arm 21 holds the radiation source 25 and the imaging table 24. In addition, handrails 27 for the subject A to hold are provided on both sides of the connection portion 22B. The radiation source 25 is an example of a "radiation source" according to the technology of the present disclosure.

The breast M of the subject A is placed on the imaging table 24. A radiation detector 26 is accommodated in the imaging table 24. The imaging table 24 is an example of an "imaging table" according to the technology of the present disclosure.

The radiation source 25 emits radiation toward the breast M placed on the imaging table 24. The radiation source 25 is an example of a "radiation source" according to the technology of the present disclosure. The radiation emitted from the radiation source 25 is transmitted through the compression plate 30 and then is incident on the breast M. The radiation detector 26 detects the radiation transmitted through the breast M and outputs a radiographic image. The radiation detector 26 is referred to as a flat panel detector (FPD). The radiation detector 26 may be an indirect conversion type that includes a scintillator converting the radiation into visible light and converts the visible light emitted from the scintillator into an electric signal or a direct conversion type that directly converts the radiation into an electric signal.

An irradiation field limiter 31 is provided between the radiation source 25 and the imaging table 24. The irradiation field limiter 31 is also referred to as a collimator and defines an irradiation field of the radiation to the imaging table 24.

A face guard 32 is attached to the radiation source accommodation portion 22A. The face guard 32 is formed of or coated with a material not transmitting the radiation and protects a face of the subject A from the radiation.

The compression plate 30 is provided between the imaging table 24 and the irradiation field limiter 31 to sandwich the breast M with the imaging table 24 and compress the breast M. The compression plate 30 is formed of a material that transmits the radiation. The compression plate 30 is disposed at a position facing the imaging table 24. In the present embodiment, the compression plate 30 has a box shape in which an upper surface side is open.

A projector 14 is accommodated in the radiation source accommodation portion 22A. The projector 14 is disposed on the rear side with respect to the radiation source 25 in the radiation source accommodation portion 22A. The projector 14 emits projection light L from the radiation source accommodation portion 22A through a mirror 14C. The projector 14 projects an image (for example, an image showing a skin line) toward an imaging surface 24A of the imaging table 24. Here, the imaging surface 24A is a surface facing the radiation source 25 on the imaging table 24. In addition, the projector 14 projects an image (for example, an image showing imaging conditions) toward a surface of the compression plate 30 facing the radiation source 25. Here, the surface of the compression plate 30 facing the radiation source 25 is the bottom plate 30A of the compression plate 30.

A moving mechanism 35 supports the compression plate 30 to be movable between the radiation source 25 and the imaging table 24. Further, a movable portion 34 is disposed between the compression plate 30 and the moving mechanism 35. The movable portion 34 is slidably held by a rail 28 provided in the moving mechanism 35. The rail 28 extends in an up-down direction.

The moving mechanism 35 includes, for example, a motor (not shown), a motor driver (not shown), and a feed screw mechanism (not shown). The motor rotates in accordance with an electric drive signal output by the motor driver and moves the compression plate 30 via the feed screw mechanism.

The compression plate 30 is attached to the movable portion 34. The movable portion 34 moves in the up-down direction together with the compression plate 30 by the moving mechanism 35. The up-down direction is functionally a direction in which the compression plate 30 moves toward the imaging table 24 (downward direction) and a direction in which the compression plate 30 moves away from the imaging table 24 (upward direction). As described above, the compression plate 30 is configured to be movable in such a manner that a distance from the imaging table 24 is changed.

Figure 3:
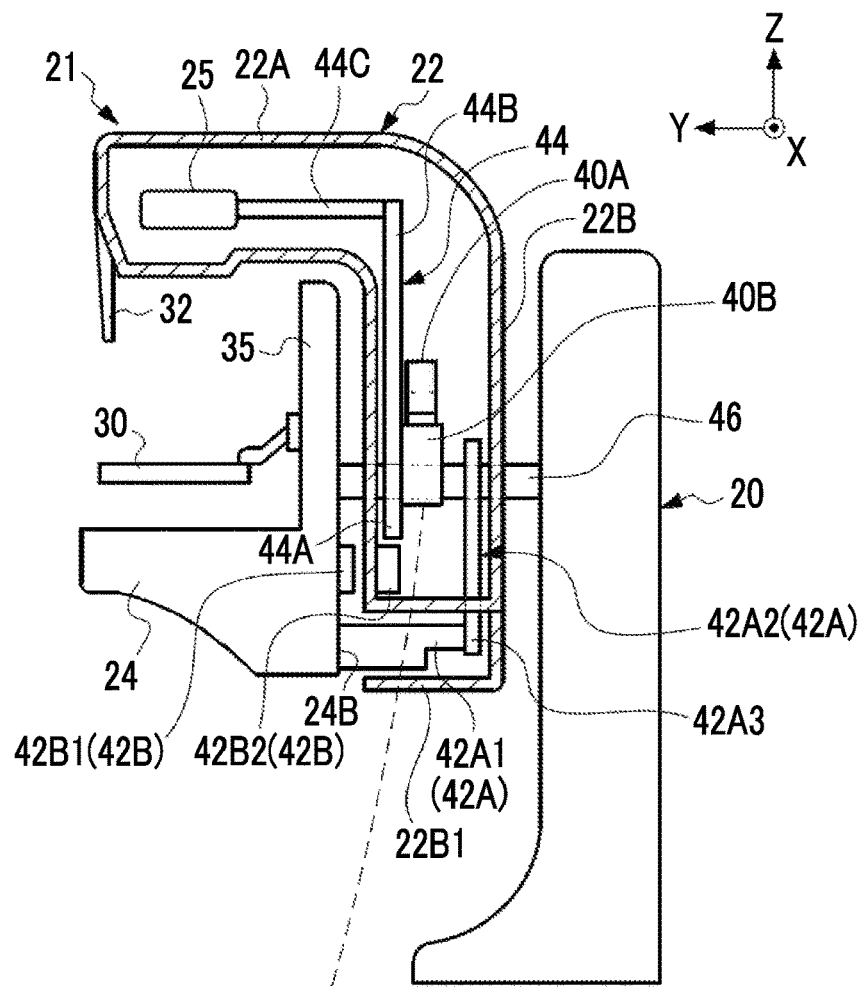
FIG. 3 is an external side view showing an example of the configuration of the mammography apparatus.
Figure 3:
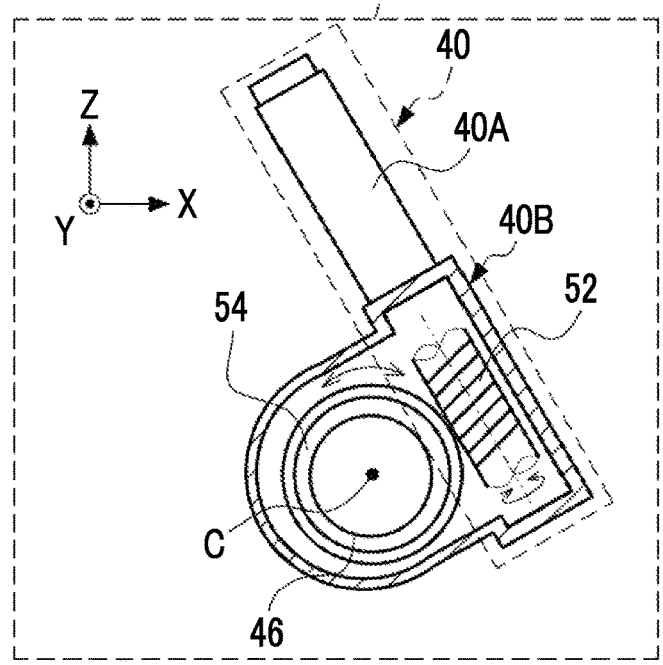

As shown in FIG. 3, the radiation source holding portion 22 is connected to the imaging table 24 via the support shaft 46. A radiation source holding frame 44 used as a holding member for holding the radiation source 25 is provided in the radiation source holding portion 22. As will be described later, the radiation source holding frame 44 is, for example, a plate-like member having a longitudinal direction in the height direction. The support shaft 46 is a cylindrical member and is inserted through a lower end portion 44A of the radiation source holding frame 44. The support shaft 46 is inserted between the radiation source holding portion 22 and the imaging table 24. An end portion of the support shaft 46 on the imaging table 24 side is held by a bearing member (not shown), and the support shaft 46 is fixed to the stand 20. The support shaft 46 is an example of a "support shaft" according to the technology of the present disclosure.

Further, the support shaft 46 is inserted between the stand 20 and the radiation source holding portion 22. Further, an end portion of the support shaft 46 on the stand 20 side is supported by a bearing member (not shown). Accordingly, the stand 20 supports the arm 21 to be rotatable about an axis of the support shaft 46.

A drive mechanism 40 and the radiation source holding frame 44 are provided inside the connection portion 22B of the radiation source holding portion 22. The drive mechanism 40 rotates the arm 21 with respect to the stand 20 about the support shaft 46. In addition, the drive mechanism 40 rotates the radiation source holding portion 22 with respect to the imaging table 24. The drive mechanism 40 is attached to the support shaft 46. The drive mechanism 40 includes a motor 40A. The drive mechanism 40 transmits a torque generated by the operation of the motor 40A to a rotating member rotatably attached to the support shaft 46 via a gearbox 40B. Accordingly, the radiation source holding portion 22 including the drive mechanism 40 rotates with respect to the support shaft 46. The drive mechanism 40 is an example of a "drive mechanism" according to the technology of the present disclosure.

Specifically, the motor 40A generates the torque by receiving a control signal from a control device (not shown) and rotating a rotor (not shown). The gearbox 40B has, for example, a housing structure, and a plurality of power transmission members including a worm 52 are accommodated in the gearbox 40B. The worm 52 is a cylindrical screw gear, and receives the torque from the motor 40A to rotate about a central axis of a cylinder as a rotation center. A worm wheel 54 is a gear that meshes with the worm 52 and is fixed to the support shaft 46. Further, the worm 52 is fixed to the housing structure of the drive mechanism 40. Accordingly, the worm 52 rotates with respect to the worm wheel 54 and the support shaft 46 with the rotation of the worm 52 about the central axis of the cylinder as the rotation center (that is, the worm 52 moves along an outer periphery of the worm wheel 54) so that the drive mechanism 40 rotates with respect to the support shaft 46. Although an example of a form in which the drive mechanism 40 rotates with respect to the support shaft 46 by a power from the motor 40A using the worm 52 and the worm wheel 54 has been described here, this is only an example. The technology of the present disclosure is established as long as the drive mechanism 40 rotates with respect to the support shaft 46 by receiving the power from the motor 40A.

A restriction mechanism 42 is provided in the arm 21. The restriction mechanism 42 comprises a first restriction mechanism 42A that restricts the rotation of the imaging table 24 with respect to the stand 20, and a second restriction mechanism 42B that restricts the rotation of the radiation source holding portion 22 with respect to the imaging table 24. As an example, the first restriction mechanism 42A and the second restriction mechanism 42B include an electromagnetic brake that utilizes a magnet that generates a magnetic force by energization and a magnetizing plate. The magnetizing plate is formed of a magnetic material to which the magnet can be magnetically attracted. The first restriction mechanism 42A and the second restriction mechanism 42B are disposed below the lower end portion 44A of the radiation source holding frame 44 in the vertical direction in order to avoid interference with the radiation source holding portion 22. Here, as described above, the support shaft 46 is inserted through the lower end portion 44A of the radiation source holding frame 44. In addition, the radiation source 25 is attached to an upper end portion 44B of the radiation source holding frame 44. That is, the first restriction mechanism 42A and the second restriction mechanism 42B are provided on a side opposite to the radiation source 25 with respect to the support shaft 46. The first restriction mechanism 42A is an example of a "first restriction mechanism" according to the technology of the present disclosure, and the second restriction mechanism 42B is an example of a "second restriction mechanism" according to the technology of the present disclosure.

The drive mechanism 40 is disposed above the first restriction mechanism 42A in the vertical direction. In other words, the drive mechanism 40 is disposed on the radiation source 25 side with respect to the first restriction mechanism 42A.

In addition, the first restriction mechanism 42A is provided at a position facing the motor 40A of the drive mechanism 40 with the support shaft 46 interposed therebetween. As described above, in order to avoid interference with the radiation source holding frame 44, the first restriction mechanism 42A is disposed below the lower end portion 44A of the radiation source holding frame 44 in the vertical direction (a direction along the Z direction shown in FIG. 3). On the other hand, the drive mechanism 40 is disposed above the first restriction mechanism 42A in the vertical direction with the support shaft 46 interposed therebetween.

The first restriction mechanism 42A comprises, for example, a magnet 42A1 and a magnetizing plate 42A2. The magnet 42A1 is provided at a position facing the stand 20 on a rear end surface 24B of the imaging table 24. The magnetizing plate 42A2 is a plate-like member fixed to the support shaft 46, and a part thereof is accommodated in the connection portion 22B. A lower end portion 42A3 of the magnetizing plate 42A2 projects downward from the connection portion 22B. Further, the magnetizing plate 42A2 is covered with a cover member 22B 1 provided in the connection portion 22B. In addition, a part of the magnet 42A1 is also covered with the cover member 22B 1. In this way, a part of the first restriction mechanism 42A is accommodated in the radiation source holding portion 22. The magnet 42A1 and the magnetizing plate 42A2 are magnetically attracted to each other so that the stand 20 and the imaging table 24 are fixed to each other. Accordingly, the rotation of the imaging table 24 with respect to the stand 20 is restricted.

The second restriction mechanism 42B comprises, for example, a magnet 42B1 and a magnetizing plate 42B2. The magnet 42B1 is provided at a position facing the radiation source holding portion 22 on the rear end surface 24B of the imaging table 24. The magnetizing plate 42B2 is disposed on the imaging table 24 side inside the connection portion 22B. The magnet 42B 1 and the magnetizing plate 42B2 are magnetically attracted to each other so that the radiation source holding portion 22 and the imaging table 24 are fixed to each other. Accordingly, the rotation of the radiation source holding portion 22 with respect to the imaging table 24 is restricted. Here, an example of a form in which the first restriction mechanism 42A and the second restriction mechanism 42B have the magnet and the magnetizing plate has been described, but this is only an example. The technology of the present disclosure is established as long as the restriction mechanism 42 can restrict the rotation between the imaging table 24, the stand 20, and the radiation source holding portion 22.

The radiation source holding frame 44 is a frame member for holding the radiation source 25 at a position facing the imaging table 24. The radiation source holding frame 44 is, for example, a plate-like member having a longitudinal direction in the height direction (a direction along the Z direction shown in FIG. 3). The support shaft 46 is attached to the lower end portion 44A of the radiation source holding frame 44. Further, the radiation source 25 is attached to the upper end portion 44B of the radiation source holding frame 44 via an attachment member 44C. The drive mechanism 40 is attached to the radiation source holding frame 44.

As described above, the drive mechanism 40 rotates with respect to the support shaft 46. Accordingly, the radiation source holding frame 44, which is integrated with the drive mechanism 40 and is rotatably attached to the support shaft 46, rotates about the lower end portion 44A. As a result, the arm 21 rotates with respect to the stand 20, and the radiation source holding portion 22 rotates with respect to the imaging table 24.

Figure 4:
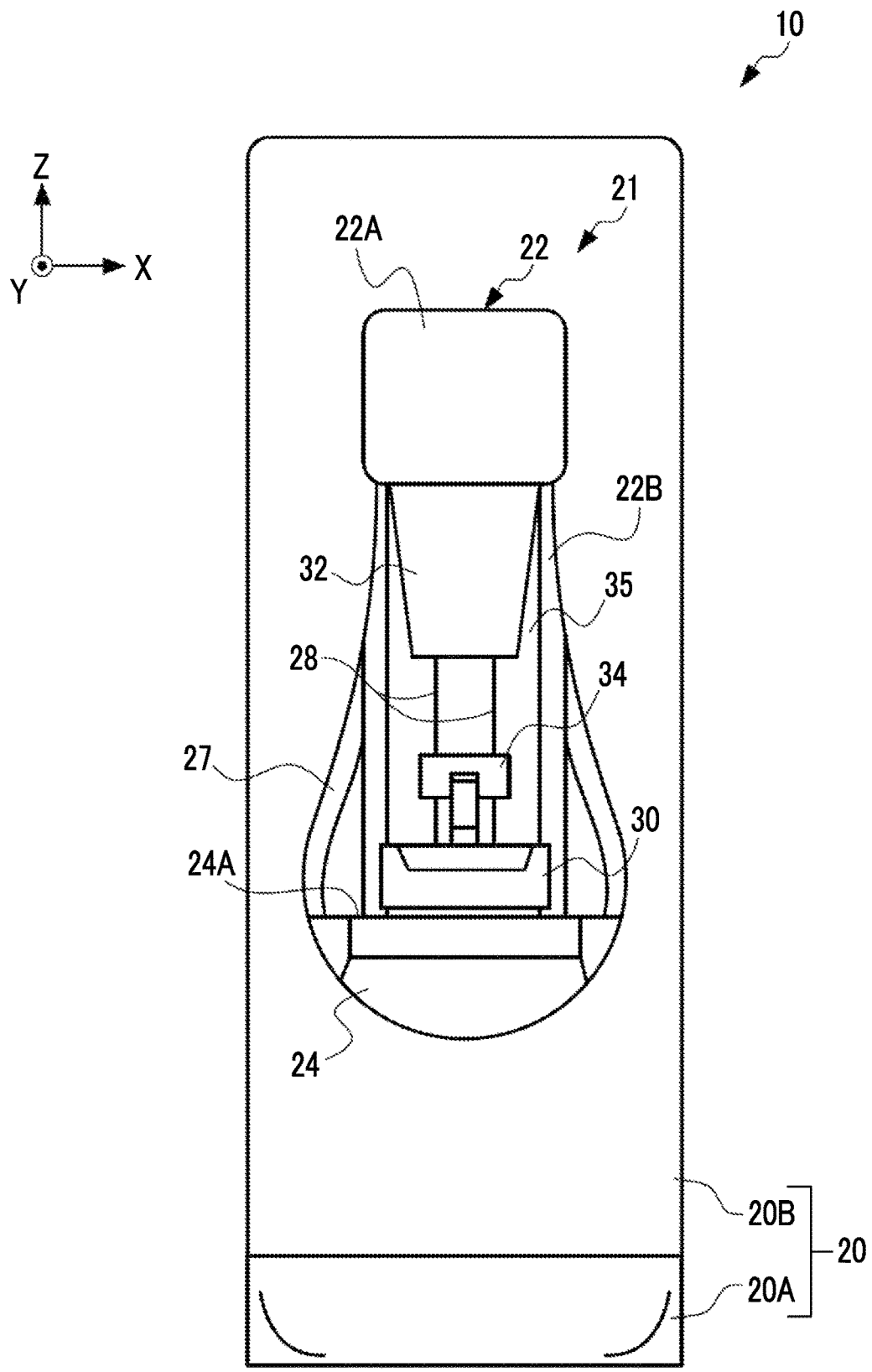
FIG. 4 is an external front view showing an example of the configuration of the mammography apparatus.

Next, a rotational operation of the arm 21 in the mammography apparatus 10 according to the present embodiment will be described with reference to FIGS. 4 to 6. First, in a case where cranio-caudal (CC) imaging is performed in which the breast M is compressed from a cranio-caudal direction of the subject A (see FIG. 2) and imaged, as shown in FIG. 4, imaging is performed in a state in which the arm 21 is fixed at a position where the arm 21 is not rotated with respect to the stand 20 (that is, a position where the imaging table 24 and the radiation source 25 face each other in the vertical direction, hereinafter simply referred to as a "reference position"). That is, the rotation of the arm 21 is restricted by the restriction mechanism 42. Specifically, in the first restriction mechanism 42A, the magnet 42A1 and the magnetizing plate 42A2 are attracted to each other so that the imaging table 24 is fixed to the stand 20. Further, in the second restriction mechanism 42B, the magnet 42B1 and the magnetizing plate 42B2 are attracted to each other so that the radiation source holding portion 22 is fixed to the imaging table 24. In this state, the CC imaging is performed.

Figure 5:
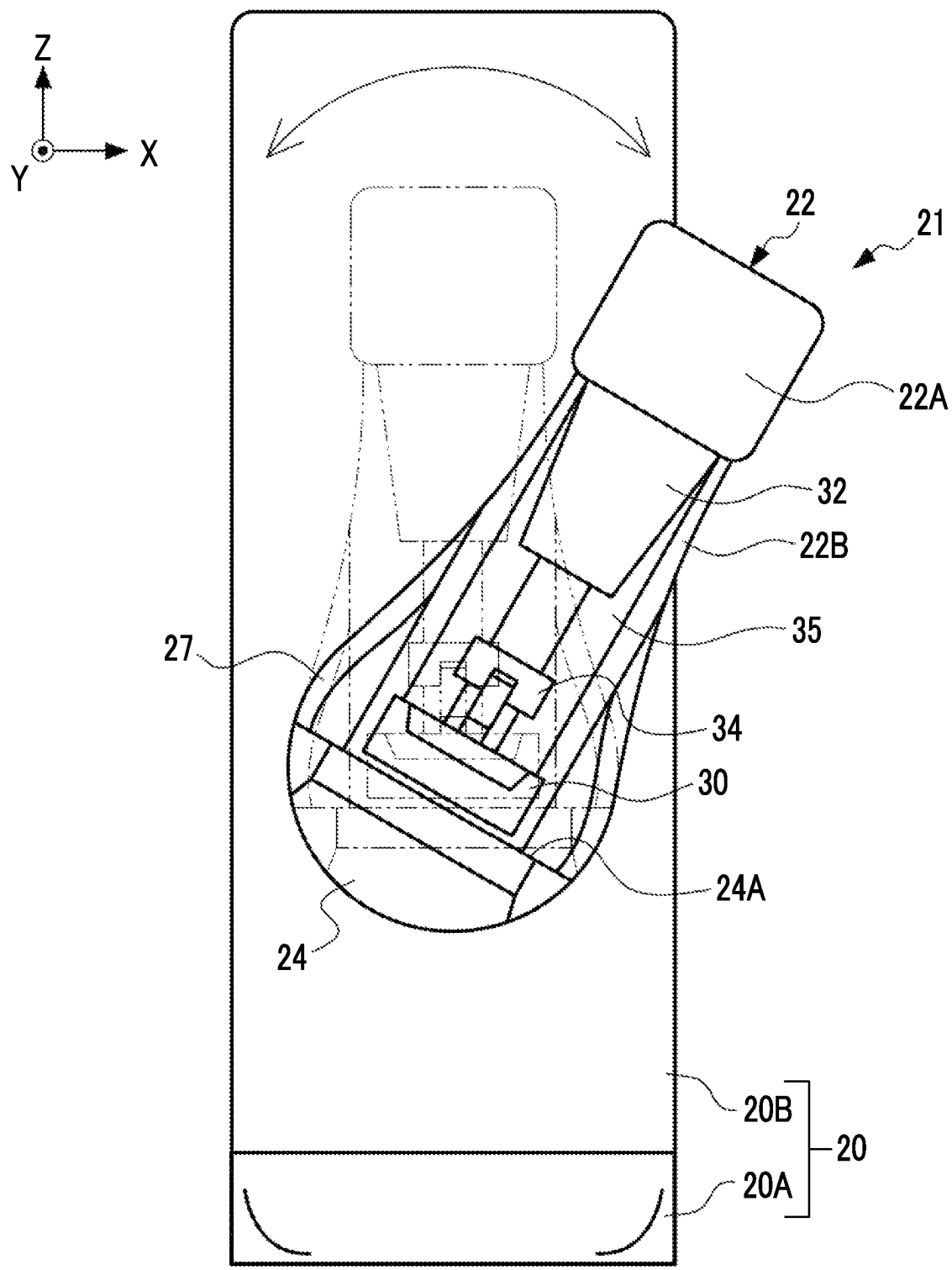
FIG. 5 is an external front view showing an example of a rotational operation of the mammography apparatus.

Next, in a case where medio-lateral (MLO) imaging in which the breast M is compressed from a direction inclined with respect to the cranio-caudal direction of the subject A (see FIG. 2) and imaged is performed, as shown in FIG. 5, imaging is performed in a state in which the arm 21 is rotated with respect to the stand 20. That is, first, in a state in which, in the second restriction mechanism 42B, the magnet 42B1 and the magnetizing plate 42B2 are attracted to each other so that the imaging table 24 is fixed to the radiation source holding portion 22, and in the first restriction mechanism 42A, the magnet 42A1 and the magnetizing plate 42A2 are separated from each other so that rotation restriction of the imaging table 24 with respect to the stand 20 is released, the arm 21 is rotated with respect to the stand 20 and a posture of the arm 21 is inclined with respect to the reference position by a predetermined angle. Then, in a state in which the arm 21 is set in a target posture, in the first restriction mechanism 42A, the magnet 42A1 and the magnetizing plate 42A2 are attracted to each other so that the rotation of the arm 21 with respect to the stand 20 is restricted. In this state, the MLO imaging is performed.

Figure 6:
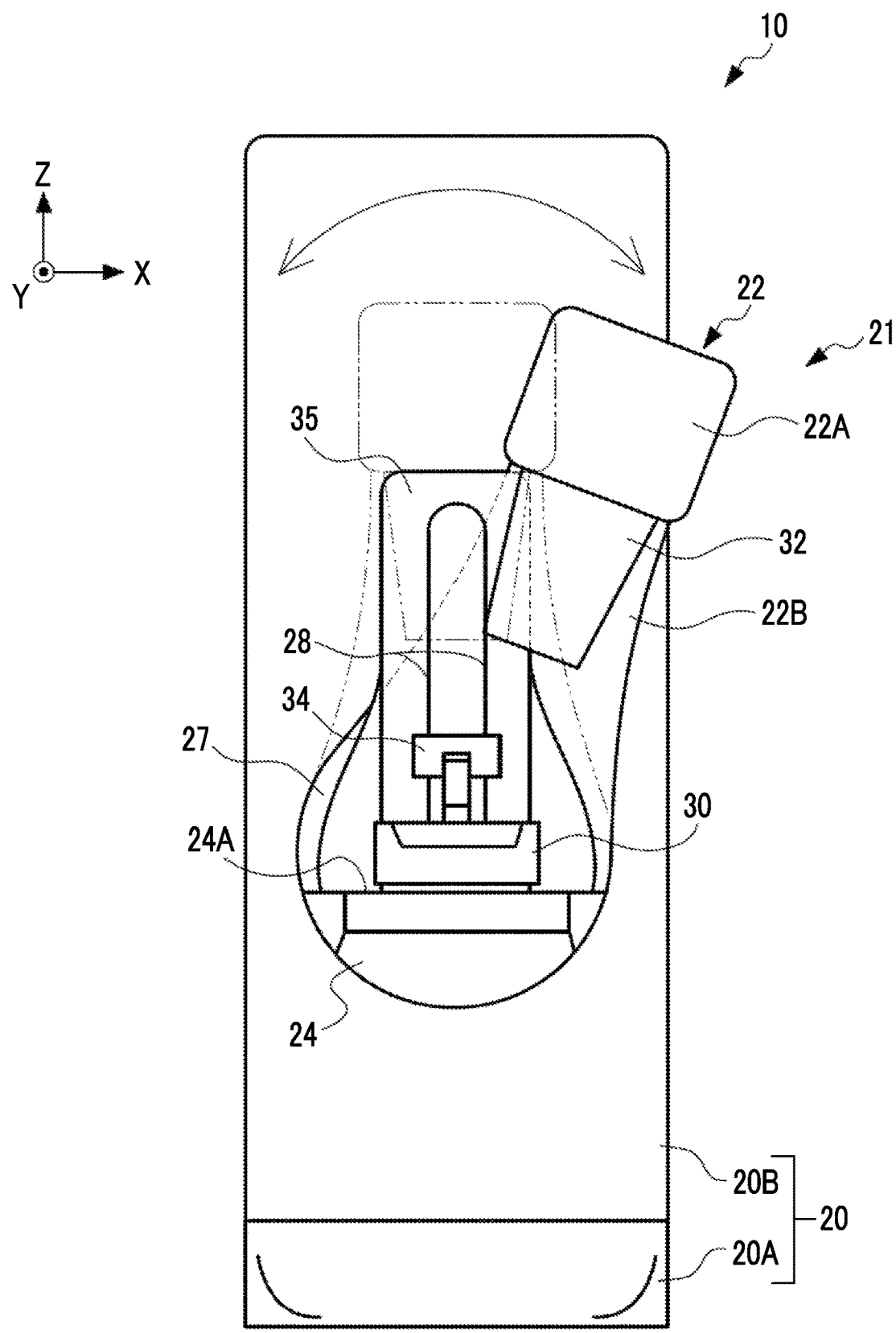
FIG. 6 is an external front view showing an example of the rotational operation of the mammography apparatus.

Further, in a case where tomosynthesis imaging in which imaging is performed by moving the radiation source 25 to each of a plurality of irradiation positions is performed, as shown in FIG. 6, the imaging is performed in a state in which the radiation source holding portion 22 of the arm 21 is rotated with respect to the imaging table 24. That is, in the tomosynthesis imaging, first, in a state in which, in the second restriction mechanism 42B, the magnet 42B1 and the magnetizing plate 42B2 are separated from each other so that rotation restriction of the imaging table 24 with respect to the radiation source holding portion 22 is released, and in the first restriction mechanism 42A, the magnet 42A1 and the magnetizing plate 42A2 are attracted to each other so that the imaging table 24 is fixed to the stand 20, the radiation source holding portion 22 is rotated by the drive mechanism 40. At this time, in the second restriction mechanism 42B, the magnet 42B1 and the magnetizing plate 42B2 are separated from each other so that the imaging table 24 and the radiation source holding portion 22 are spaced apart from each other, and only the radiation source holding portion 22 rotates with respect to the imaging table 24 and the stand 20. In other words, the arm 21 can rotate the radiation source holding portion 22 with respect to the imaging table 24 by rotating the radiation source holding portion 22 about the axis of the support shaft 46 independently of the imaging table 24. In this state, the tomosynthesis imaging is performed.

In the tomosynthesis imaging, for example, a rotation range in which the radiation source holding portion 22 rotates during imaging is predetermined, and a plurality of images are captured while the radiation source holding portion 22 rotates within the rotation range. Accordingly, a plurality of radiographic images having different irradiation angles with respect to the imaging table 24 can be obtained. Image reconstruction processing is performed based on the plurality of radiographic images thus captured to generate a tomographic image of the breast.

In a case where the rotational operation is performed by the arm 21 as described above, the radiation source 25 is located at a position distant from a rotation center of the radiation source holding portion 22 and the radiation source 25 is relatively heavy among constituent components accommodated in the radiation source holding portion 22. Therefore, a rotational moment of the radiation source holding portion 22 around the support shaft 46 tends to be large. Further, in a case where the drive mechanism 40 and the restriction mechanism 42 are disposed in the radiation source holding portion 22, the rotational moment around the support shaft 46 may be larger depending on a positional relationship between the drive mechanism 40, the restriction mechanism 42, and the radiation source 25. As a result, the load applied to the drive mechanism 40 becomes larger.

Figure 7:
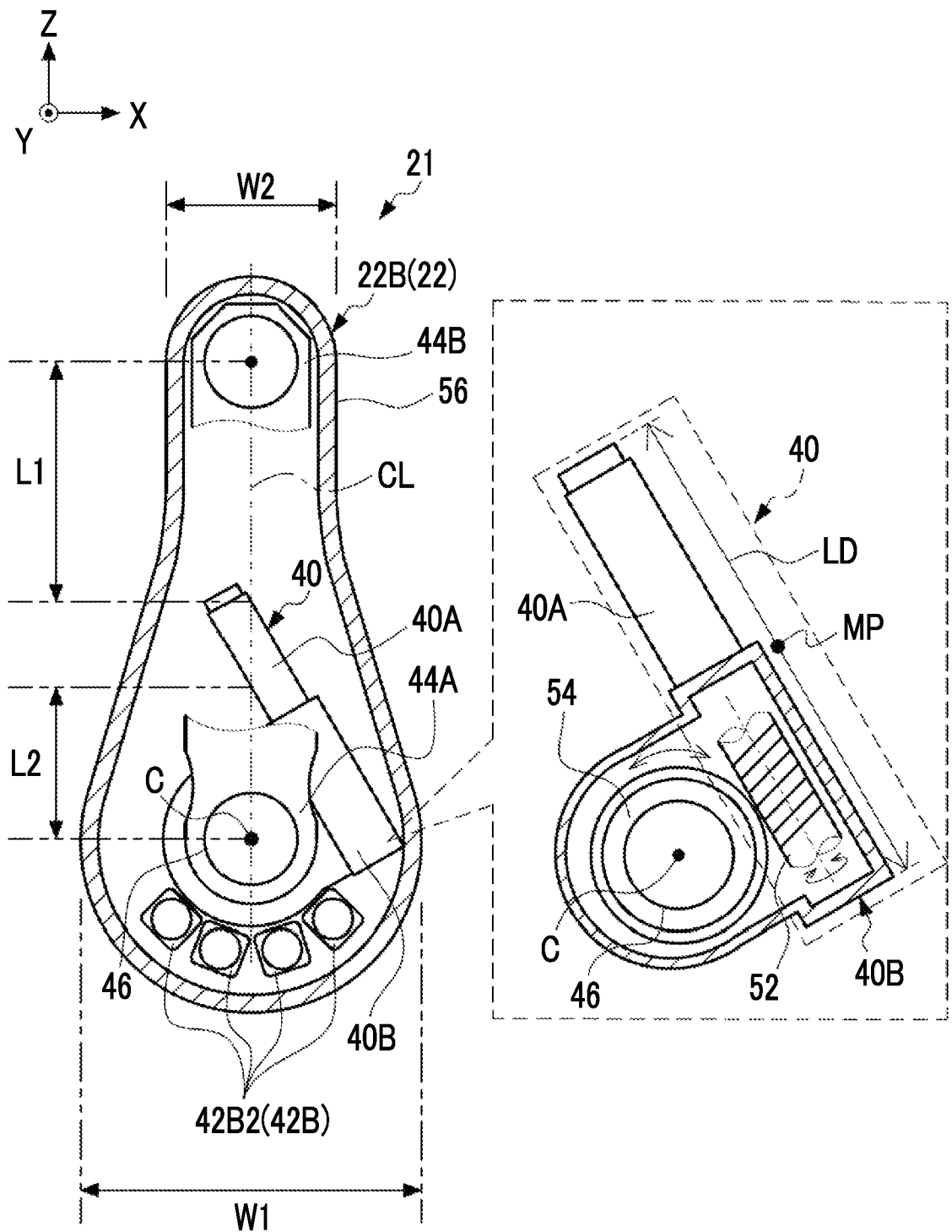
FIG. 7 is a schematic view showing an example of an internal structure of an arm body.

Therefore, as shown in FIG. 7, in a case where a center line CL is assumed in the radiation source holding portion 22 as viewed from a direction in which the support shaft 46 is extended (the Y direction shown in FIG. 7, hereinafter also simply referred to as a "support shaft direction"), the drive mechanism 40 intersects the center line CL. That is, a part of components constituting the drive mechanism 40 intersects the center line CL. Here, the center line CL is a straight line extending in a direction connecting a rotation center C of the support shaft 46 and the radiation source 25 and is a center line of the arm 21. In other words, the center line CL means a straight line that is parallel to the vertical direction and passes through the rotation center C of the support shaft 46 at the reference position of the arm 21. Substantially, the center line CL is a center line that bisects the width direction of the radiation source holding portion 22 of the arm 21 at the reference position. The center line CL is an example of a "center line" according to the technology of the present disclosure.

In an example shown in FIG. 7, the drive mechanism 40 is disposed in a posture in which a longitudinal direction LD thereof is inclined with respect to the center line CL. As described above, in the drive mechanism 40, the motor 40A is connected to the gearbox 40B. Therefore, the drive mechanism 40 has a shape having the longitudinal direction LD along a direction in which the motor 40A is connected to the gearbox 40B. As described above, the drive mechanism 40 is inclined with respect to the center line CL, and in this state, the drive mechanism 40 intersects the center line CL. More specifically, the motor 40A of the drive mechanism 40 intersects the center line CL.

The drive mechanism 40 is located on the rotation center C side with respect to the radiation source 25 side in the center line CL direction. Specifically, the drive mechanism 40 is disposed at a position where the shortest distance L2 between the drive mechanism 40 and the rotation center C along the center line CL direction is shorter than the shortest distance L1 between the drive mechanism 40 and the radiation source 25 along the center line CL direction.

The magnetizing plate 42B2 constituting the second restriction mechanism 42B or a region between the magnetizing plates 42B2 intersects the center line CL. In the example shown in FIG. 7, an example in which four magnetizing plates 42B2 are provided is shown. The four magnetizing plates 42B2 are disposed side by side at equal intervals along a circumferential direction below the support shaft 46. In addition, although an example of a form in which four magnetizing plates 42B2 are provided is given here, this is only an example, and the number of the magnetizing plates 42B2 may be one or more and three or less, or may be five or more.

The radiation source holding portion 22 comprises a housing 56. The housing 56 has a housing structure that forms an outer shape of the radiation source holding portion 22. The housing 56 accommodates the drive mechanism 40 and the radiation source holding frame 44. The housing 56 has a shape in which a width in a direction orthogonal to the center line CL (a distance in the X direction shown in FIG. 7) becomes narrower from the lower end portion 44A to the upper end portion 44B of the radiation source holding frame 44 as viewed from the support shaft direction. In the example shown in FIG. 7, the housing 56 has a maximum width W1 on the lower side in the vertical direction, and the width becomes narrower toward the upper side in the vertical direction (that is, toward the upper end portion 44B side of the radiation source holding frame 44). The housing 56 has a width W2 on the upper side in the vertical direction, and the width W2 is smaller than the width W1.

The drive mechanism 40 is disposed so as to fit inside the housing 56. An intersection position where the drive mechanism 40 intersects the center line CL is located on the radiation source 25 side with respect to a center position MP in the longitudinal direction LD of the drive mechanism 40. As described above, the width of the housing 56 becomes narrower from the support shaft 46 side to the radiation source 25 side. The fact that the drive mechanism 40 is disposed so as to intersect the center line CL on the radiation source 25 side in the longitudinal direction LD means that the drive mechanism 40 intersects the center line CL in a region where the width of the housing 56 is narrowed. That is, the drive mechanism 40 is disposed inside the housing 56 in accordance with the shape of the housing 56.

As described above, in the mammography apparatus 10 according to the present embodiment, the radiation source holding portion 22 is provided with the drive mechanism 40. In the arm 21, the restriction mechanism 42 is disposed on a side opposite to the radiation source 25 with respect to the support shaft 46. In addition, the drive mechanism 40 is disposed on the radiation source 25 side with respect to the restriction mechanism 42. Further, in a case where the center line CL extending in a direction connecting the radiation source 25 and the rotation center C of the support shaft 46 is assumed, the drive mechanism 40 is disposed in a state of intersecting the center line CL. In general, in the mammography apparatus 10, the center of gravity of the radiation source holding portion 22 is preferably close to the center of the support shaft 46 from the viewpoint of reducing the rotational moment of the arm 21 around the support shaft 46. In the arm 21, a radiation source 25, which is heavier than other components of the arm 21, is provided at an end portion on a side opposite to the support shaft 46. In such an arm 21, the restriction mechanism 42 is disposed on a side opposite to the radiation source 25 with respect to the support shaft 46. Accordingly, the position of the center of gravity in the center line CL direction can be brought closer to the rotation center C of the support shaft 46 as compared to a case where the restriction mechanism 42 is not provided. Further, in a case where the drive mechanism 40 is provided in the radiation source holding portion 22, the drive mechanism 40 is disposed in a state of intersecting the center line CL. Accordingly, the position of the center of gravity of the radiation source holding portion 22 in the width direction can be brought closer to the center line CL. As a result, the rotational moment of the arm 21 around the support shaft 46 is reduced as compared to a case where the arrangement of the restriction mechanism 42 and the drive mechanism 40 in the present configuration is not adopted in the arm 21.

Figure 8:
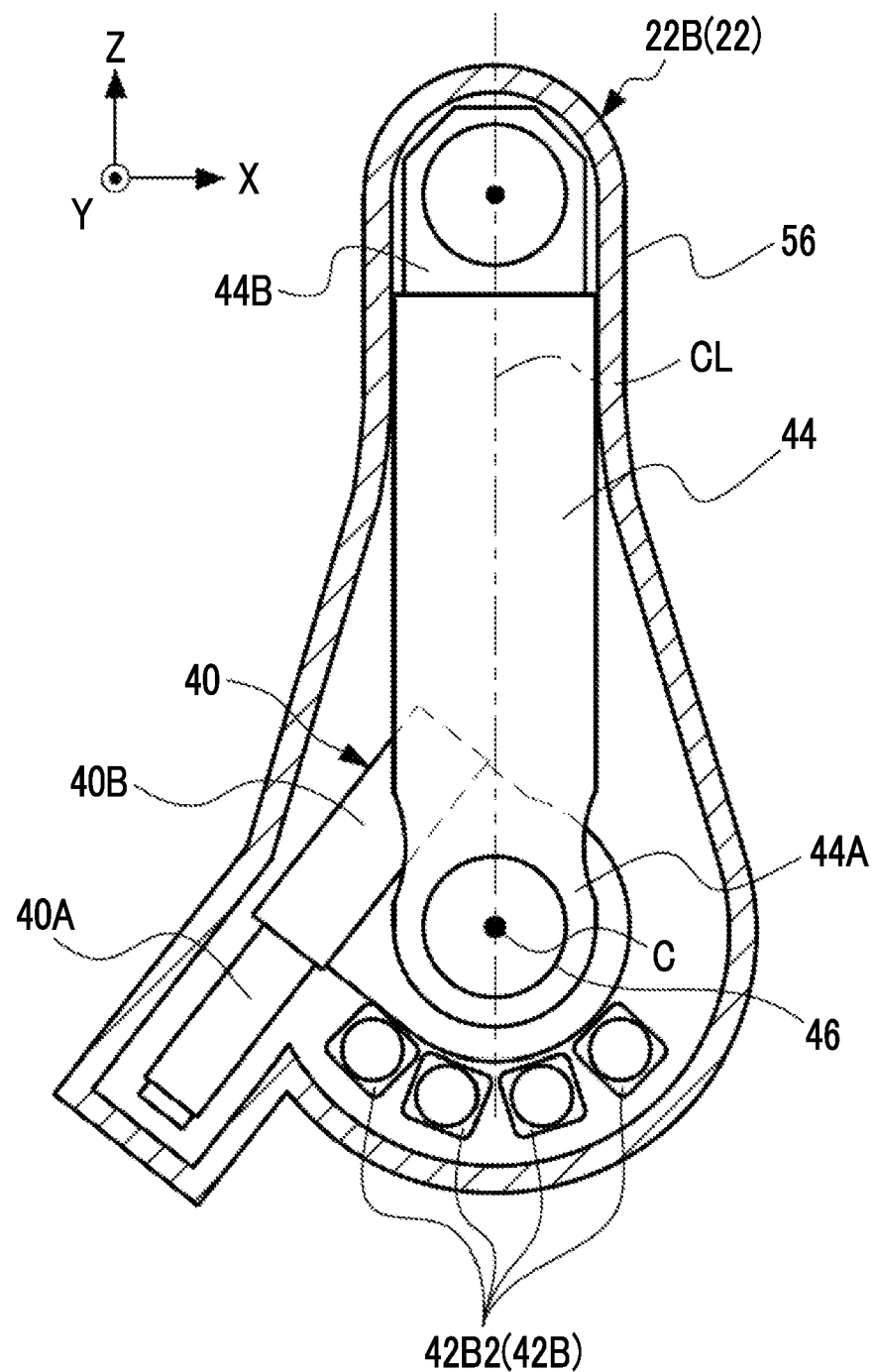
FIG. 8 is a schematic view showing an example of the internal structure of the arm body as a comparative example.

For example, as shown in FIG. 8 as a comparative example, a case where the drive mechanism 40 is disposed at a position that does not intersect the center line CL and does not interfere with the restriction mechanism 42 is considered. In this case, since the drive mechanism 40 does not intersect the center line CL, the position of the center of gravity of the radiation source holding portion 22 in the width direction is located farther from the center line CL as compared to the present embodiment. As a result, the rotational moment of the arm 21 around the support shaft 46 is increased, and the load applied to the drive mechanism 40 is increased. On the other hand, in the mammography apparatus 10 according to the present embodiment, since the restriction mechanism 42 and the drive mechanism 40 are disposed as described above, the rotational moment of the arm 21 around the support shaft 46 is reduced.

Further, in the mammography apparatus 10 according to the present embodiment, the motor 40A of the drive mechanism 40 and the center line CL intersect each other. By making the motor 40A which is relatively heavy in the drive mechanism 40 intersect the center line CL, the center of gravity of the radiation source holding portion 22 in the width direction can be brought closer to the center line CL. Accordingly, the rotational moment of the arm 21 around the support shaft 46 is reduced as compared to a case where the motor 40A and the center line CL do not intersect each other.

In addition, in the mammography apparatus 10 according to the present embodiment, in the direction of the center line CL, the shortest distance L2 between the drive mechanism 40 and the rotation center C of the support shaft 46 is set to be smaller than the shortest distance L1 between the drive mechanism 40 and the radiation source 25. The fact that the shortest distance L2 is shorter than the shortest distance L1 means that the drive mechanism 40 is disposed relatively close to the support shaft 46. Accordingly, the position of the center of gravity in the direction of the center line CL can be brought closer to the center of the support shaft 46. As a result, the rotational moment of the arm 21 around the support shaft 46 is reduced as compared to a case where the drive mechanism 40 is closer to the radiation source 25 side.

In general, in the radiation source holding portion 22, a distance from the support shaft 46 is longer to the radiation source 25 than to the restriction mechanism 42, and the radiation source 25 is heavier than the restriction mechanism 42 in many cases. Therefore, the center of gravity of the radiation source holding portion 22 in the center line CL direction is closer to the radiation source 25 side. In a case where the drive mechanism 40 is provided in such a radiation source holding portion 22, by disposing the drive mechanism 40 close to the support shaft 46, it is possible to bring the position of the center of gravity in the center line CL direction closer to the center of the support shaft 46. Accordingly, the rotational moment of the arm 21 around the support shaft 46 is reduced.

Further, in the mammography apparatus 10 according to the present embodiment, the motor 40A of the drive mechanism 40 and the restriction mechanism 42 are disposed at positions facing each other with the support shaft 46 interposed therebetween. As a result, the center of gravity can be brought closer to the center of the support shaft 46 as compared to a case where the motor 40A and the restriction mechanism 42 do not face each other with the support shaft 46 interposed therebetween. As a result, the rotational moment of the arm 21 around the support shaft 46 is reduced.

Further, in the mammography apparatus 10 according to the present embodiment, the drive mechanism 40 has the longitudinal direction LD, and the drive mechanism 40 is disposed in a posture in which the longitudinal direction LD is inclined with respect to the center line CL. In a case where the drive mechanism 40 has the longitudinal direction LD, and the drive mechanism 40 is disposed in a posture in which the longitudinal direction LD is inclined with respect to the center line CL, the center of gravity of the radiation source holding portion 22 in the width direction can be brought closer to the center line CL as compared to a case where the longitudinal direction LD is disposed in parallel with the center line CL. Accordingly, the rotational moment of the arm 21 around the support shaft 46 is reduced.

Further, in the mammography apparatus 10 according to the present embodiment, the drive mechanism 40 is accommodated in the radiation source holding portion 22, and a part of the first restriction mechanism 42A is accommodated in the radiation source holding portion 22. Accordingly, it is suppressed that a part of the first restriction mechanism 42A is exposed to the outside. For example, a part of the magnet 42A1 of the first restriction mechanism 42A does not come into direct contact with the outside (for example, peripheral components of the mammography apparatus 10), so that the safety is further improved. In addition, for example, adhesion of dust or the like to an attraction portion of the magnetizing plate 42A2 is suppressed, and a decrease in the magnetizing force is suppressed.

Further, in the mammography apparatus 10 according to the present embodiment, the radiation source holding portion 22 has the housing 56 that accommodates the radiation source 25 and the drive mechanism 40. In a case where the housing 56 is viewed from the support shaft direction, the width of the housing 56 in a direction orthogonal to the center line CL is narrowed from the support shaft 46 side toward the radiation source 25 side. The intersection position where the drive mechanism 40 intersects the center line CL is located on the radiation source 25 side with respect to the center position MP in the longitudinal direction LD. Since the housing 56 is narrowed toward the radiation source 25 side, by setting the intersection position between the drive mechanism 40 and the center line CL to the radiation source 25 side, it is easy to dispose a part of the drive mechanism 40 in a portion having a narrow width of the housing 56. Accordingly, downsizing of the radiation source holding portion 22 is realized.

In addition, in the mammography apparatus 10 according to the present embodiment, the second restriction mechanism 42B that restricts the rotation of the radiation source holding portion 22 with respect to the imaging table 24 is provided. The second restriction mechanism 42B is provided on a side opposite to the radiation source 25 with respect to the support shaft 46. As a result, the restriction mechanism 42 becomes heavier as compared to a case where only the first restriction mechanism 42A is provided in the arm 21. According to the present configuration, even in this case, the position of the center of gravity in the center line CL direction can be brought closer to the rotation center C of the support shaft 46 as described above. As a result, the rotational moment of the arm 21 around the support shaft 46 is reduced.

First Modification Example

The above embodiment has been described with an example of a form in which an aspect of the intersection between the drive mechanism 40 and the center line CL is such that the drive mechanism 40 and the center line CL intersect each other by inclining the motor 40A side of the drive mechanism 40 to the left side with respect to the center line CL, but the technology of the present disclosure is not limited thereto.

Figure 9:
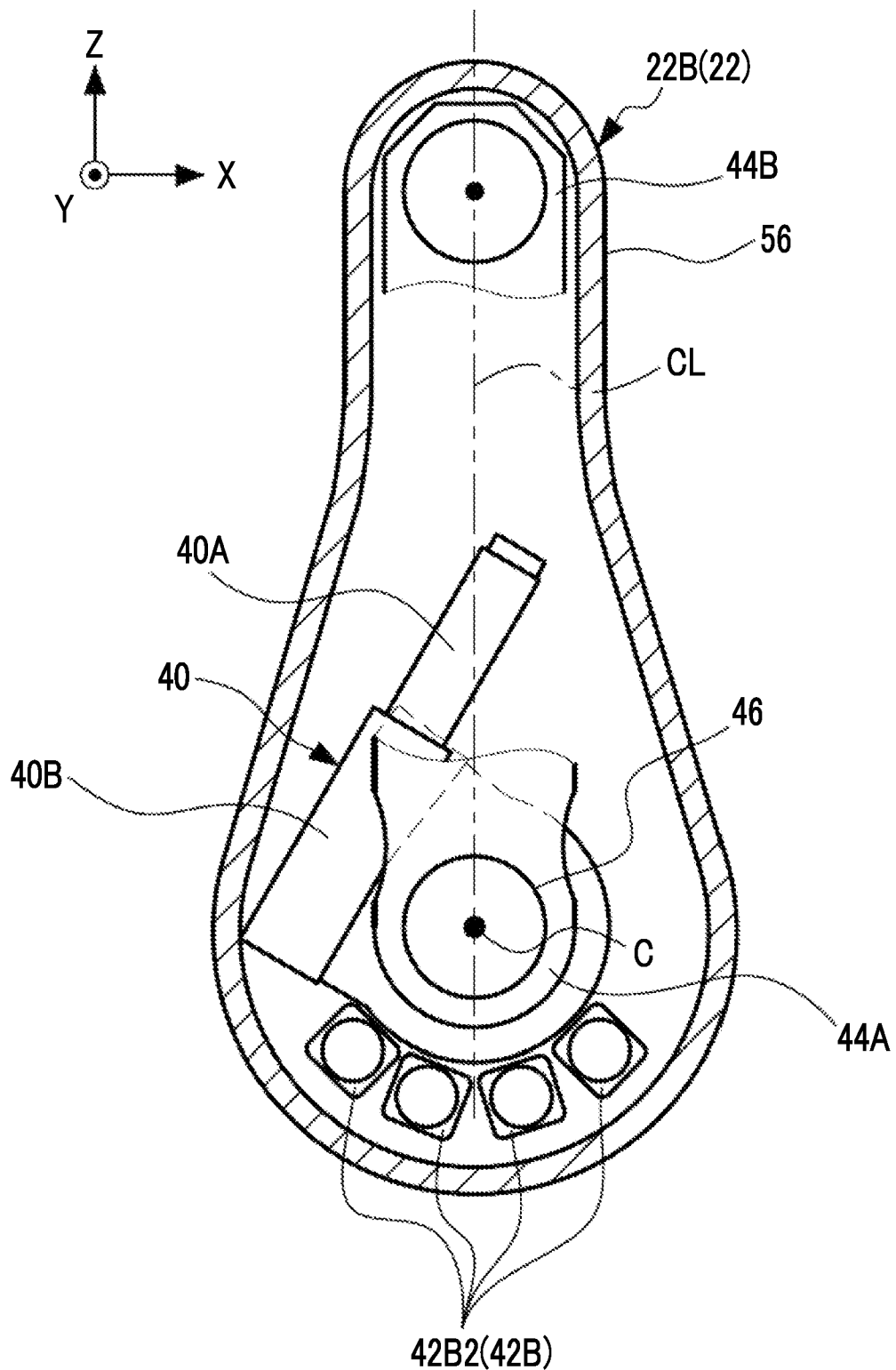
FIG. 9 is a schematic view showing a modification example of the internal structure of the arm body.

As shown in FIG. 9, in the first modification example, the drive mechanism 40 and the center line CL intersect each other by inclining the motor 40A side of the drive mechanism 40 to the right side with respect to the center line CL. In other words, with respect to the arrangement of the drive mechanism 40 according to the embodiment, the drive mechanism 40 according to the first modification example is disposed at a position line-symmetrical with respect to the center line CL. Accordingly, the position of the center of gravity of the radiation source holding portion 22 in the width direction can be brought closer to the center line CL. As a result, in the radiation source holding portion 22, the rotational moment of the radiation source holding portion 22 around the support shaft 46 is reduced as compared to a case where the arrangement of the drive mechanism 40 in the present configuration is not adopted.

Second Modification Example

Figure 10:
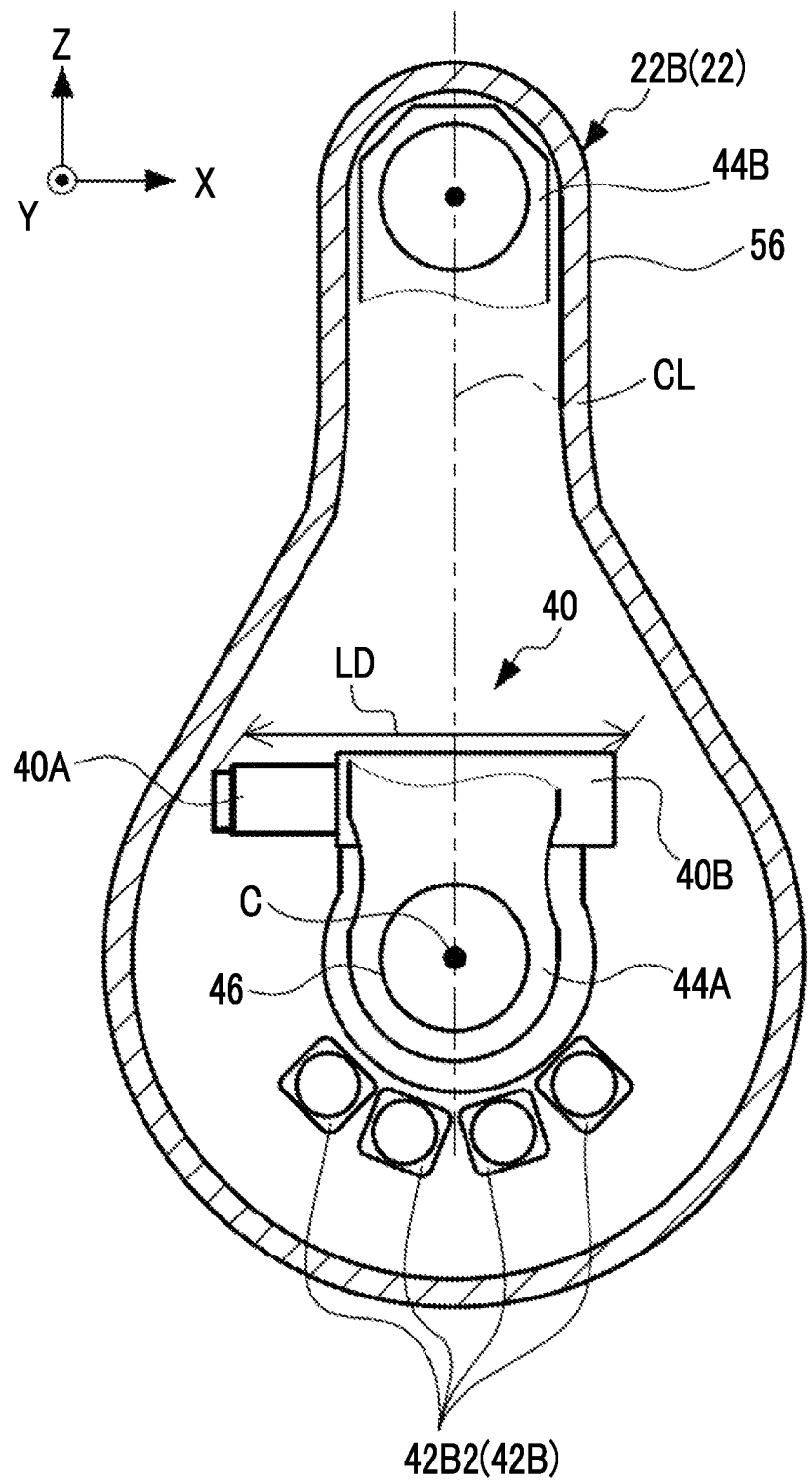
FIG. 10 is a schematic view showing a modification example of the internal structure of the arm body.

The above embodiment has been described with an example of a form in which the drive mechanism 40 intersects the center line CL in a manner inclined with respect to the center line CL, but the technology of the present disclosure is not limited thereto. In the second modification example, the drive mechanism 40 intersects the center line CL in a manner orthogonal to the center line CL. As shown in FIG. 10, the drive mechanism 40 is orthogonal to the center line CL. In other words, the longitudinal direction LD of the drive mechanism 40 is orthogonal to the center line CL. Accordingly, the position of the center of gravity of the radiation source holding portion 22 in the width direction can be brought closer to the center line CL. As a result, in the radiation source holding portion 22, the rotational moment of the radiation source holding portion 22 around the support shaft 46 is reduced as compared to a case where the arrangement of the drive mechanism 40 in the present configuration is not adopted.

Figure 11:
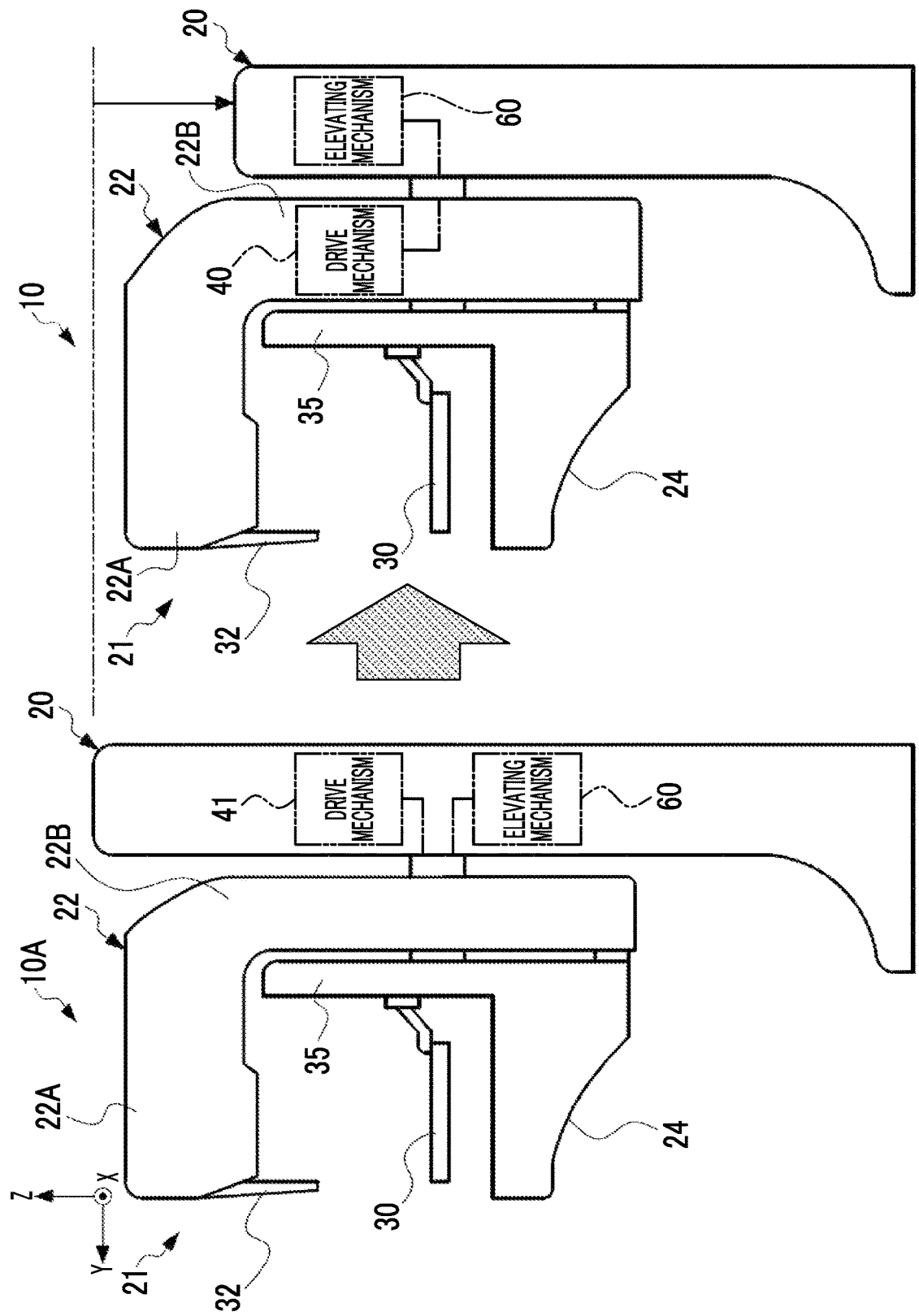
FIG. 11 is a schematic view for explaining downsizing of the mammography apparatus.

In the mammography apparatus 10 according to the first embodiment and each modification example, the drive mechanism 40 is disposed in the arm 21. On the other hand, as shown on the left side in FIG. 11, in a conventionally known mammography apparatus 10A, the stand 20 comprises an elevating mechanism 60 and a drive mechanism 41. The elevating mechanism 60 moves the arm 21 in the vertical direction. The drive mechanism 41 rotates the arm 21 with respect to the stand 20 or rotates the radiation source holding portion 22 with respect to the imaging table 24. As shown on the right side in FIG. 11, in the mammography apparatus 10 according to the present embodiment, the drive mechanism 40 is disposed in the radiation source holding portion 22. Further, the elevating mechanism 60 is disposed in the stand 20.

As described above, in the mammography apparatus 10 according to the present embodiment and each modification example, the elevating mechanism 60 for raising and lowering the arm 21 is disposed in the stand 20. In addition, the drive mechanism 40 is disposed in the radiation source holding portion 22. As a result, a size of the stand 20 can be reduced as compared to a case where both the drive mechanism 40 for rotating the arm 21 and the elevating mechanism 60 are provided in the stand 20.

In the above embodiment, an example of a form in which the arm 21 rotates with respect to the stand 20 by fixing the support shaft 46 to the stand 20 and rotating the drive mechanism 40 with respect to the support shaft 46 has been shown, but the technology of the present disclosure is not limited thereto. For example, a configuration in which the support shaft 46 is rotated by the drive mechanism 40 may be adopted. In this case, in a case where the radiation source holding portion 22 rotates with respect to the imaging table 24, a configuration in which transmission of a torque is switched between the imaging table 24 and the radiation source holding portion 22 (for example a clutch mechanism for switching between transmission and non-transmission of a torque of the support shaft 46) is adopted.

In addition, the above embodiment has been described with an example of a form in which in the second restriction mechanism 42B, the magnet 42B1 is provided in the imaging table 24 and the magnetizing plate 42B2 is provided in the radiation source holding portion 22, but the technology of the present disclosure is not limited to thereto. The magnetizing plate 42B2 may be provided in the imaging table 24, and the magnet 42B1 may be provided in the radiation source holding portion 22.

In addition, as described above, an example of a form in which in the first restriction mechanism 42A, the magnet 42A1 is provided in the imaging table 24 and the magnetizing plate 42A2 is attached to the support shaft 46 has been described, but the technology of the present disclosure is not limited to thereto. For example, the magnetizing plate 42A2 may be attached to the stand 20. Further, for example, the magnetizing plate 42A2 may be provided in the imaging table 24, and the magnet 42A1 may be attached to the support shaft 46.

In addition, the above embodiment has been described with an example of a form in which the first restriction mechanism 42A and the second restriction mechanism 42B are provided in the restriction mechanism 42, but the technology of the present disclosure is not limited thereto. The magnetizing plates 42A1 and 42B1 may be integrated to reduce the number of components, and the numbers and positions of the magnets 42A2 and 42B2 may be appropriately adjusted in consideration of an attractive force.

The above-described contents and illustrated contents are detailed descriptions of parts related to the technology of the present disclosure, and are merely examples of the technology of the present disclosure. For example, the above descriptions related to configurations, functions, operations, and advantages effects are descriptions related to examples of configurations, functions, operations, and advantages effects of the parts related to the technology of the present disclosure. Therefore, it is needless to say that unnecessary parts may be deleted, or new elements may be added or replaced with respect to the above-described contents and illustrated contents within a scope not departing from the spirit of the technology of the present disclosure. In order to avoid complication and easily understand the parts according to the technology of the present disclosure, in the above-described contents and illustrated contents, common technical knowledge and the like that do not need to be described to implement the technology of the present disclosure are not described.

All documents, patent applications, and technical standards described in the present specification are incorporated in the present specification by reference to the same extent as in a case where each document, patent application, and technical standard are specifically and individually noted to be incorporated by reference.

Furthermore, the following appendices will be disclosed in relation to the above-described embodiment.

APPENDIX 1

A mammography apparatus comprising: an arm composed of a radiation source holding portion that holds a radiation source, and an imaging table on which a breast is placed; and a stand that is connected to the arm via a support shaft and supports the arm to be rotatable about an axis of the support shaft, in which the arm is capable of rotating the radiation source holding portion with respect to the imaging table by rotating the radiation source holding portion about the axis of the support shaft independently of the imaging table, the arm is provided with a drive mechanism including a motor that rotationally drives the radiation source holding portion, and a first restriction mechanism that restricts rotation of the imaging table about the axis of the support shaft, the first restriction mechanism is disposed on a side opposite to the radiation source with respect to the support shaft, and the drive mechanism is disposed on a radiation source side with respect to the first restriction mechanism and in a case where a center line of the arm extending in a direction connecting the radiation source and a center of the support shaft is assumed, the drive mechanism is disposed so as to intersect the center line.

APPENDIX 2

The mammography apparatus according to appendix 1, in which the motor and the center line intersect each other.

APPENDIX 3

The mammography apparatus according to appendix 1 or 2, in which in a direction of the center line, a shortest distance between the drive mechanism and the center of the support shaft is shorter than a shortest distance between the drive mechanism and the radiation source.

APPENDIX 4

The mammography apparatus according to any one of appendices 1 to 3, in which the motor and the first restriction mechanism are disposed at positions facing each other with the support shaft interposed therebetween.

APPENDIX 5

The mammography apparatus according to any one of appendices 1 to 4, in which the drive mechanism has a longitudinal direction and is disposed in a posture in which the longitudinal direction is inclined with respect to the center line.

APPENDIX 6

The mammography apparatus according to any one of appendices 1 to 5, in which the drive mechanism is accommodated in the radiation source holding portion, and at least a part of the first restriction mechanism is accommodated in the radiation source holding portion.

APPENDIX 7

The mammography apparatus according to any one of appendices 1 to 6, in which the radiation source holding portion has a housing that accommodates the radiation source and the drive mechanism, in a case where the housing is viewed from a direction in which the support shaft extends, a width of the housing in a direction orthogonal to the center line is narrowed from a support shaft side toward the radiation source side, and an intersection position where the drive mechanism intersects the center line is located on the radiation source side with respect to a center position in the longitudinal direction.

APPENDIX 8

The mammography apparatus according to any one of appendices 1 to 7, in which an elevating mechanism for raising and lowering the arm is disposed in the stand.

APPENDIX 9

The mammography apparatus according to any one of appendices 1 to 8, in which the arm is further provided with a second restriction mechanism that restricts rotation of the radiation source holding portion with respect to the imaging table and that is disposed on a side opposite to the radiation source with respect to the support shaft.

What is claimed is:
1. A mammography apparatus comprising:
an arm composed of a radiation source holding portion that holds a radiation source, and an imaging table on which a breast is placed; and
a stand that is connected to the arm via a support shaft and supports the arm to be rotatable about an axis of the support shaft,
wherein the arm is capable of rotating the radiation source holding portion with respect to the imaging table by rotating the radiation source holding portion about the axis of the support shaft independently of the imaging table, the arm is provided with a drive mechanism including a motor that rotationally drives the radiation source holding portion, and a first restriction mechanism that restricts rotation of the imaging table about the axis of the support shaft, the first restriction mechanism is disposed on a side opposite to the radiation source with respect to the support shaft, and the drive mechanism is disposed on a radiation source side with respect to the first restriction mechanism and in a case where a center line of the arm extending in a direction connecting the radiation source and a center of the support shaft is assumed, the drive mechanism is disposed so as to intersect the center line.

2. The mammography apparatus according to claim 1, wherein the motor and the center line intersect each other.

3. The mammography apparatus according to claim 1, wherein in a direction of the center line, a shortest distance between the drive mechanism and the center of the support shaft is shorter than a shortest distance between the drive mechanism and the radiation source.

4. The mammography apparatus according to claim 1, wherein the motor and the first restriction mechanism are disposed at positions facing each other with the support shaft interposed therebetween.

5. The mammography apparatus according to claim 1, wherein the drive mechanism has a longitudinal direction and is disposed in a posture in which the longitudinal direction is inclined with respect to the center line.

6. The mammography apparatus according to claim 1, wherein the drive mechanism is accommodated in the radiation source holding portion, and at least a part of the first restriction mechanism is accommodated in the radiation source holding portion.

7. The mammography apparatus according to claim 5, wherein the radiation source holding portion has a housing that accommodates the radiation source and the drive mechanism, in a case where the housing is viewed from a direction in which the support shaft extends, a width of the housing in a direction orthogonal to the center line is narrowed from a support shaft side toward the radiation source side, and an intersection position where the drive mechanism intersects the center line is located on the radiation source side with respect to a center position in the longitudinal direction.

8. The mammography apparatus according to claim 1, wherein an elevating mechanism for raising and lowering the arm is disposed in the stand.

9. The mammography apparatus according to claim 1, wherein the arm is further provided with a second restriction mechanism that restricts rotation of the radiation source holding portion with respect to the imaging table and that is disposed on a side opposite to the radiation source with respect to the support shaft.

* * * * *